United States Patent [19]

Defaye et al.

[11] Patent Number: 5,798,342

[45] Date of Patent: Aug. 25, 1998

[54] USE OF NATURAL CYCLODEXTRINS AND THEIR DERIVATIVES FOR THE SOLUBILIZATION OF PLATELET ANTI-AGGREGATING AGENTS FROM THE FAMILY OF GINKGOLIDES

[75] Inventors: Jacques Defaye, St. Ismier; Valérie Laine, St. Jean de Bournay; Florence Djedaini-Pilard, Etampes; Bruno Perly, La Verriere, all of France

[73] Assignee: Commissariat a l'Energie Atomique, Paris, France

[21] Appl. No.: 711,265

[22] Filed: Sep. 9, 1996

[30] Foreign Application Priority Data

Sep. 20, 1995 [FR] France .................. 95 11040

[51] Int. Cl.$^6$ .................. A61K 31/715; A61K 31/335; A61K 31/365
[52] U.S. Cl. .................. 514/58; 424/195.1; 514/185; 514/783; 536/103
[58] Field of Search .................. 424/195.1, 439; 514/54, 58, 185, 783; 536/103

[56] References Cited

U.S. PATENT DOCUMENTS

| | | | |
|---|---|---|---|
| 5,180,588 | 1/1993 | Shinmen et al. | 424/439 |
| 5,211,953 | 5/1993 | Shinmen et al. | 424/439 |
| 5,240,732 | 8/1993 | Ueda | 426/597 |
| 5,322,688 | 6/1994 | Schwabe | 424/195.1 |
| 5,399,348 | 3/1995 | Schwabe | 424/195.1 |
| 5,512,286 | 4/1996 | Schwabe | 424/195.1 |

OTHER PUBLICATIONS

Szejtli, J. "Medicinal Applications of Cyclodextrins", *Medicinal Research Reviews*, vol. 14(3): 353–386, (1994).

*Primary Examiner*—John Kight
*Assistant Examiner*—Howard C. Lee
*Attorney, Agent, or Firm*—Oblon, Spivak, McClelland, Maier & Neustadt, P.C.

[57] ABSTRACT

The invention relates to the use of natural cyclodextrins and their derivatives for the solubilization of platelet anti-aggregating agents from the family of Ginkgolides.

The cyclodextrins used comply with the formula:

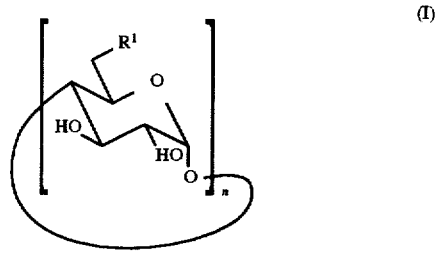

(I)

in which n is equal to 6, 7 or 8 and the $R^1$, which can be the same or different, represent OH or $SR^2$ with $R^2$ representing a group derived from a monosaccharide or an oligosaccharide.

The Ginkgolide is preferably Ginkgolide B.

24 Claims, 2 Drawing Sheets

USE OF NATURAL CYCLODEXTRINS AND THEIR DERIVATIVES FOR THE SOLUBILIZATION OF PLATELET ANTI-AGGREGATING AGENTS FROM THE FAMILY OF GINKGOLIDES

The present invention relates to a solubilization process in an aqueous medium for an antagonizing agent of the aggregation factor of platelets belonging to the family of Ginkgolides. Ginkgolides are chemical compounds having 6 cycles with 5 joined members or groups.

Figure 1:
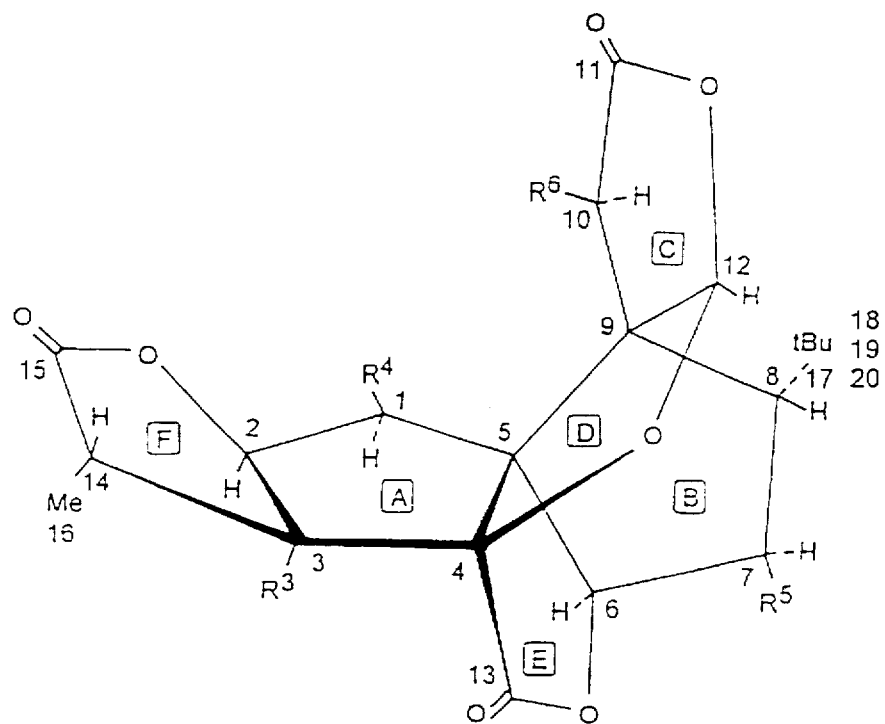

FIG. 1 shows the developed formula of said Ginkgolides. As can be seen the Ginkgolides have a tetrahydrofuran cycle (D), 2 cyclopentane cycles with a common carbon (A and B) forming a spiro-(4,4)-nonane and 3 γ-lactones (C, E and F). Ginkgolides are extracted from leaves of Ginkgo bilobe, have a unique cage-shaped structure and a strong potential of biological activities. The great diversity of these activities in the series of Ginkgolides would appear to be solely due to substitution differences and conformational changes.

In these Ginkgolides, whose formula is given in FIG. 1, $R^3$, $R^4$, $R^5$ and $R^6$ can represent H or OH and $R^4$ can also represent a lower alkoxy group such as methoxy (OMe) or ethoxy (OEt).

Table 1 groups certain known Ginkgolides complying with this formula with the nature of the substituents $R^3$, $R^4$, $R^5$ and $R^6$.

TABLE 1

| Compound No. | Ginkgolide | Nomenclature 1 HB | $R^3$ | $R^4$ | $R^5$ | $R^6$ |
|---|---|---|---|---|---|---|
| 1 | A | BN 52020 | OH | H | H | OH |
| 2 | B | BN 52021 | OH | OH | H | OH |
| 3 | C | BN 52022 | OH | OH | OH | OH |
| 4 | J | BN 52024 | OH | H | OH | OH |
| 5 | M | BN 52023 | H | OH | OH | OH |
| 6 | synthetic | BN 50580 | OH | OMe | H | OH |
| 7 | synthetic | BN 50585 | OH | OEt | H | OH |

The majority Ginkgolides are compounds 1, 2 and 3, forms A, B and C, the other forms (J, M), compounds 4 and 5, being rare. The compound having the most interesting pharmacological properties is Ginkgolide B (compound 2) with 3 closed lactone cycles.

Ginkgolide B has formed the object of a considerable amount of research in various fields (Bracquet, P., "Ginkgolides : Chemistry, Biology, Pharmacology and Clinical Perspectives", 1 and 2; J. R. Prous Science Publishers Barcelona 1988). Moreover, complete retrosynthesis was carried out by Corey (Corey, E. J., Kang M. C., Ghosh A. K., Houpis I. N.; J. Am. Chem. Soc., 1988, 110 649–651). Ginkgolide B has interesting pharmacological properties and would appear to demonstrate an antagonizing activity against the aggregation factor of platelets (anticoagulant), which plays a key part in the inflammatory process. It therefore has an anticoagulating activity. In vitro, pharmacological research has revealed that the effectiveness of Ginkgolide B was closely linked with the pH and that the anti-platelet activating factor or PAF activity was increased in an acid medium (Braquet, P, Op. Cit. 1, 11–23). This result is clearly related with the existence of three lactone groups which can be hydrolyzed, which leads to the opening of the cycles. These processes are reversible because, as has been demonstrated by Braquet, the acidification of basic solutions of Ginkgolide B always regenerates the starting Ginkgolide B without any deterioration in the molecular structure. This important point has been confirmed by NMR (cf. the thesis of Oussama ZEKRI, Rennes University, 1994). The authors demonstrated the presence of 8 possible forms, whose existence is closely dependent on the pH value. Thus, three pKa values were determined at 7.14, 8.60 and 11.90. Under physiological conditions: physiological phosphate buffer solution (PBS) and pH 7.39, the solubility of Ginkgolide B is 0.2 mM and the NMR study revealed the presence of 4 different forms, the closed form (active form) representing 34% thereof at 25° C. This percentage decreases when the temperature increases.

Ginkgolide B can be parenterally administered. Due to its low solubility at acid or neutral pH, it is solubilized at pH=8.75 to a concentration of 20 mg/mL (C=47 mM) in the presence of 10 mg/mL of mannitol. The NMR study of the proton at 500 MHz of this solution revealed the presence of 5 open forms having more than 99% Ginkgolide B. The totally closed form, i.e. the only active form, is in a negligible proportion, i.e. a concentration below 0.1 mM. Moreover, it was shown by conductometry, that although the opening of the lactones is relatively fast ($\approx$10 min.), their closing is slow ($\geq$3 h-cf. the thesis of Oussama ZEKRI, Rennes University, 1994). It can therefore be said that in the present injection form, the anit-PAF active form is extremely low, whereas the injected Ginkgolide quantity is high. To solve this problem one approach, which forms the object of the present invention, was to find appropriate molecules having a high solubility in an aqueous medium at physiological pH, in order to solubilize Ginkgolides such as Ginkgolide B in the aqueous medium, whilst retaining the maximum of the active form, i.e. the closed form of Ginkgolide.

The present invention specifically relates to the use of natural cyclodextrins and certain of their derivatives, in order to solubilize and protect in an aqueous medium anti-PAF agents of the Ginkgolide type by the inclusion thereof in said cyclodextrins.

Cyclodextrins or cyclomaltooligosaccharides are compounds having a natural origin formed by the connection of 6, 7 or 8 glucose units bonded in α-(1→4). Numerous works have revealed that these cyclodextrins could form inclusion complexes with hydrophobic molecules and thus permit the solubilization of these molecules in aqueous media. Numerous applications have been proposed for taking advantage of this phenomenon, particularly in the pharmaceutical sector, as is described by D. Duchêne in the work entitled "Cyclodextrins and their industrial uses", chapter 6, pp 213 to 257, Editions de Sante, 1987. Pharmaceutical compositions using cyclodextrins have also been marketed in Japan, Italy and more recently in France, e.g. by Pierre Fabre Medicament for Brexin, which is an inclusion complex of Piroxicam in β-cyclodextrin.

According to the invention, the solubilization process in an aqueous medium of an antagonizing agent of the platelet aggregation factor belonging to the family of Cinkgolides consists of combining said agent with a cyclodextrin of formula:

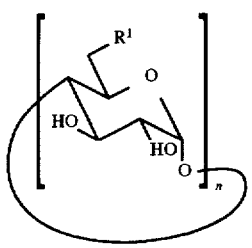

(I)

in which n is equal to 6, 7 or 8 and the $R^1$ which can be the same or different, represent OH or $SR^2$, with $R^2$ representing a group derived from a monosaccharide or an oligosaccharide, in order to form therewith an inclusion complex soluble in water.

In the aforementioned formula (I), $R^2$ can comply with the formula:

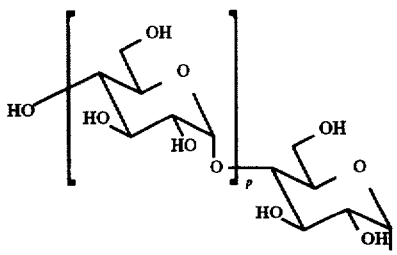

(II)

in which p is equal to 0 or an integer from 1 to 5.

According to the invention, the antagonizing agents of the platelet aggregation factor, hereinafter called anti-PAF agents, are compounds belonging to the family of Ginkgolides. They can comply with the formula given in FIG. 1, in which $R^3$, $R^5$ and $R^6$, which can be the same or different, represent H or OH, and $R^4$ represents H, OH or an alkoxy group with 1 to 5 carbon atoms.

The alkoxy groups used can in particular be methoxy and ethoxy groups.

The invention preferably applies to the anti-PAF agent constituted by Ginkgolide B complying with formula (III), in which $R^3$, $R^4$ and $R^6$ represent OH and $R^5$ represents H.

According to a first embodiment of the invention, the cyclodextrin is a natural cyclodextrin complying with the formula (I) with all the $R^1$ representing OH. Preferably, in this embodiment, n is equal to 7.

According to a second embodiment of the invention, use is made of a branched cyclodextrin, i.e. a cyclodextrin complying with formula (I), in which a single $R^1$ represents $SR^2$, the other $R^1$ being identical and representing OH.

In this second embodiment, $R^2$ is preferably the α-maltosyl or β-maltosyl group, namely the group complying with formula (II) with p equal to 1.

As in the first embodiment, preference is given to branched cyclodextrins of formula (I) in which n is equal to 7 or 8, the best results being obtained with n equal to 7 or 8, preferably 7.

The cyclodextrin derivatives used in this second embodiment of the invention can be prepared in the manner described in EP-A-403 366 and FR-A-2 715 307.

The invention also relates to the inclusion complexes of an antagonizing agent of the platelet aggregation factor belonging to the family of Ginkgolides, in a cyclodextrin complying with the formula (I).

In these inclusion complexes, preference is given to the cyclodextrin of formula (I) being β-cyclodextrin (n=7) or γ-cyclodextrin (n=8) with all the $R^1$ identical and representing OH, or a β-cyclodextrin derivative in which a single $R^1$ represents $SR^2$, with $R^2$ representing the α-maltosyl or β-maltosyl group, the other $R^1$ being identical and representing OH.

The antagonizing agents included in the cyclodextrin of this complex can be Ginkgolides of formula (III) described in FIG. 1 and in table 1, in particular Ginkgolide B corresponding to formula (III with $R^3$, $R^4$ and $R^6$ representing OH and $R^5$ representing H.

These inclusion complexes can be prepared in conventional manner, e.g. by adding to a solution of the cyclodextrin of formula (I), whose pH is below 5, a concentrated Ginkgolide solution in an appropriate, organic solvent, e.g. acetone. It should be noted that the pH value of the aqueous solution is vital. Thus, at a pH below 5, the Ginkgolides, e.g. Ginkgolide B, are solely in an entirely closed form, which is the only active form in the case of Ginkgolide B. It is then possible to isolate the thus formed inclusion complex by lyophilization.

To avoid the use of an organic solvent, during the preparation of the inclusion complex, it is possible to disperse the anti-PAF agent to be included in an aqueous solution of the cyclodextrin used, whose pH is below 5, for the same reasons as described hereinbefore, and stir the suspension obtained until a clear solution is obtained. It is then possible to isolate the thus formed inclusion complex by lyophilization, as hereinbefore.

These inclusion complexes can in particular be used in pharmaceutical compositions, which also incorporate a pharmaceutically acceptable vehicle.

These pharmaceutical compositions which can be administered orally or parenterally are e.g. solutions, powders, suspensions and in particular injectable solutions. The inclusion complexes formed with Ginkgolide B and the natural or branched cyclodextrins have a solubility at an acid pH value greater than that of Ginkgolide B alone. Moreover, at higher pH values, Ginkgolide B in the form of an inclusion complex undergoes an increase in the proportion of its closed form to a significant extent compared with Ginkgolide B alone, under the same conditions. Thus, the use of natural or branched cyclodextrins makes it possible to reduce the total quantity of Ginkgolide B injected, whilst increasing the quantity of the active form, i.e. the proportion of the closed form. In other words, the inclusion complex is more efficient with respect to the PAF, whilst minimizing the risks of side effects.

Figure 2:
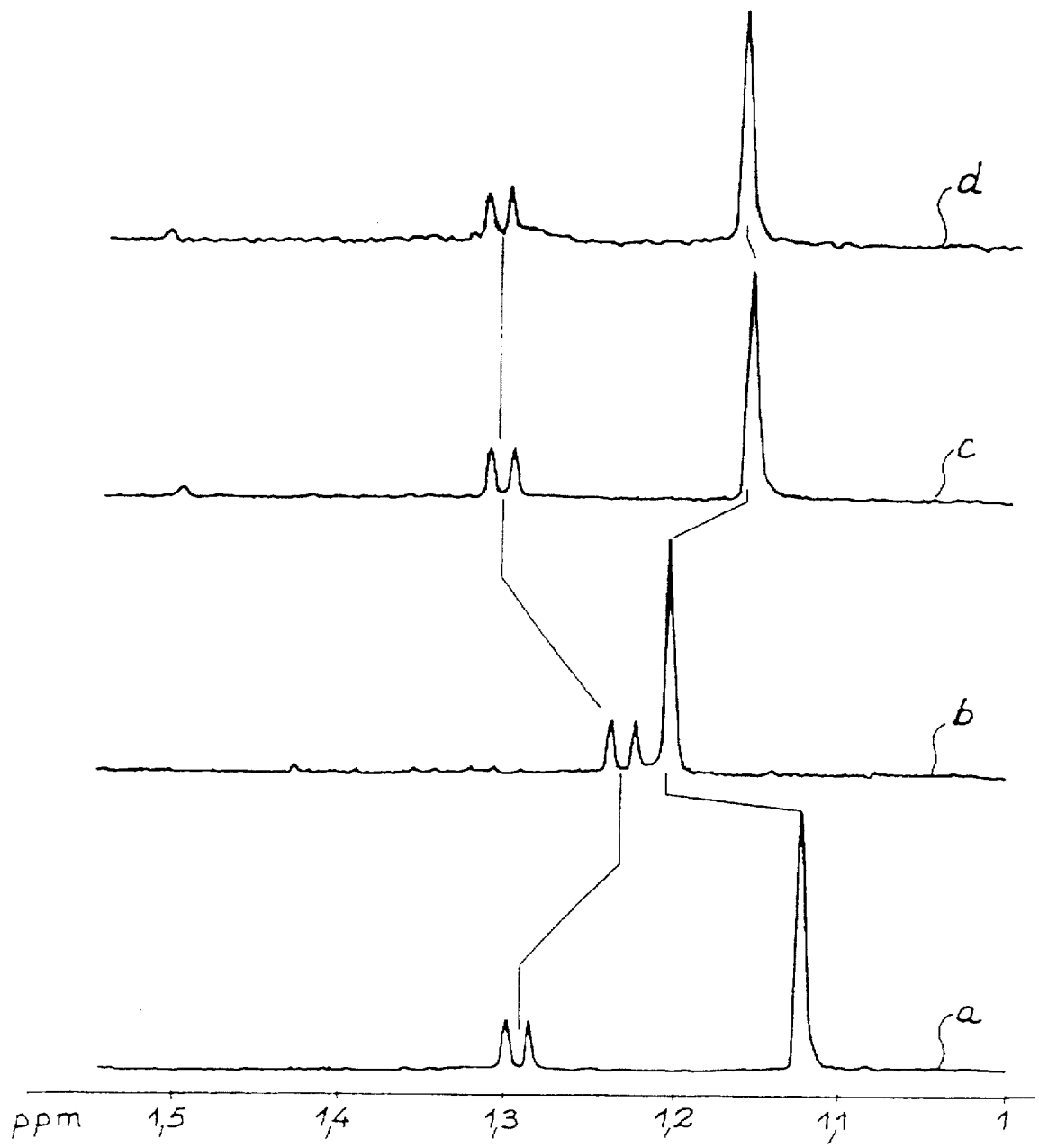

Other features and advantages of the invention can be better gathered from studying the following examples given in an illustrative and non-limitative manner and with reference to the attached drawings, wherein show:

FIG. 1, already described, the formula of the Ginkgolides used in the invention. FIG. 2 A representation of the partial nuclear magnetic resonance (NMR) spectra of the proton of inclusion complexes prepared in examples 1, 2 and 3 and of the Ginkgolide B only.

EXAMPLE 1

Preparation of an inclusion complex of Ginkgolide B with β-cyclodextrin

The starting product is a concentrated Ginkgolide B solution in a water-miscible solvent, constituted by acetone, and addition takes place of the concentrated solution quantity corresponding to 1 μmole of Ginkgolide B to 1 mL of a 10 mmole/L β-cyclodextrin solution in sterile water at pH=4.9 and at ambient temperature. The acetone is eliminated under nitrogen bubbling and the solution is lyophilized. The residual solid containing 10 μmole of β-cyclodextrin derivative and 1 μmole of Ginkgolide B is redissolved in a minimum of water at 25° C. This minimum corresponds to 1 mL of water, which indicates a maximum solubility of 1 mmole/L of Ginkgolide B in water in the presence of β-cyclodextrin at a concentration of 10 mmole/L.

The partial nuclear magnetic resonance (NMR) spectrum of the proton of this complex at a concentration of 5 mmole/L in $D_2O$, at 298 K and 500 MHz, is shown in FIG. 2 (spectrum c). FIG. 2 also shows for information purposes the partial spectrum of Ginkgolide B only (spectrum a). On comparing the two spectra, it is possible to see the modifications confirming the inclusion of Ginkgolide B in the cavity of the 13β-cyclodextrin.

It can also be seen that Ginkgolide B only exists in the inclusion complex in the closed form at pH=4.9.

It should be noted that the solubility of the inclusion complex is the same at physiological pH, namely a maximum solubility of 1 mmole/L of Ginkgolide B in the presence of 10 mmole/L of β-cyclodextrin. At physiological pH, Ginkgolide B alone exists in four different forms, whereof the closed form only represents 34% at 25° C. With the inclusion complex prepared in the manner described hereinbefore, only two different forms are observed in identical proportions including the closed form. By comparison, the maximum solubility of Ginkgolide B alone, in its closed form, is 0.2 mmole/l at pH-4.9 and 0.68 mmole/L at pH=7.39. When Ginkgolide B is in the inclusion complex form at pH 4.9 with a concentration of 1 mmole/L in the presence of 10 mmole/L of β-cyclodextrin, it has a closed form concentration which is 10 times higher than that contained in the injectable formulation (1 and 0.1 mmole/L respectively), whereas the total Ginkgolide B concentration is 40 times lower (1 and 47 mmole/L respectively).

EXAMPLE 2

Preparation of an inclusion complex of Ginkgolide B with γ-cyclodextrin

The starting product is a concentrated Ginkgolide B solution in a water-miscible solvent, constituted by acetone, and addition takes place of the concentrated solution quantity corresponding to 1 μmole of Ginkgolide B to 2 mL of 5 mmole/L γ-cyclodextrin solution in sterile water, at pH=4.9 and at ambient temperature. The acetone is eliminated under nitrogen bubbling and the solution is lyophilized. The residual solid, which contains 10 μmole of γ-cyclodextrin derivative and 1 μmole of Ginkgolide B, is redissolved in a minimum of water at 25° C. This minimum corresponds to 2 mL of water, which indicates a maximum solubility of 0.5 mmole/l of Ginkgolide B in water in the presence of γ-cyclodextrin at a concentration of 5 mmole/L.

The partial nuclear magnetic resonance (NMR) spectrum of the proton of this complex at a concentration of 5 mmole/l in $D_2O$, at 298 K and at 500 MHz is given in FIG. 2 (spectrum b). By comparing this spectrum b with spectrum a of Ginkgolide B alone, it can be seen that there are modifications to the spectrum confirming the inclusion of Ginkgolide B in the cavity of γ-cyclodextrin. It can also be seen that Ginkgolide B only exists in the closed form at pH=4.9 in the inclusion complex.

It should be noted that the solubility of the inclusion complex is the same at physiological pH, namely 0.5 mmole/L of Ginkgolide in the presence of 5 mmole/L of γ-cyclodextrin. With the inclusion complex prepared in the aforementioned manner, there are four different forms, the closed form representing 70%. When Ginkgolide B is in the form of an inclusion complex at pH 4.9 with a concentration of 0.5 mmole/L in the presence of 5 mmole/L of γ-cyclodextrin, there is a closed form concentration 5 times higher than that contained in the injectable formulation (0.5 and 0.1 mmole/L respectively), whereas the total Ginkgolide B concentration is 80 times lower (0.5 and 40 mmole/L respectively).

EXAMPLE 3

Preparation of an inclusion complex of Ginkgolide B with 6-S- α-maltosyl-6-thiocyclomaltoheptaose.

The starting product is a concentrated Ginkgolide B solution in a water miscible solvent, constituted by acetone, and addition takes place of the concentrated solution quantity corresponding to 1 μmole of Ginkgolide B, to 1 mL of a 10 mmole/L solution of β-cyclodextrin derivative, 6-S-α-maltosyl-6-thiocyclomaltoheptaose, in sterile water, at pH=4.9 and at ambient temperature. The acetone is eliminated under nitrogen bubbling and the solution is lyophilized. The residual solid containing 10 μmole of β-cyclodextrin derivative and 1 μmole of Ginkgolide B is redissolved in a minimum of water at 25° C. This minimum corresponds to 500 ul of water, which indicates a maximum solubility of 2 mmole/L of Ginkgolide B in water, in the presence of said β-cyclodextrin derivative at a concentration of 20 mmole/L.

The partial nuclear magnetic resonance (NMR) spectrum of the proton of this complex at a concentration of 5 mmole/L in $D_2O$, at 298 K and 500 MHz is shown in FIG. 2 (spectrum d). On comparing spectrum d with spectrum a, the spectrum modifications can be seen which confirm the inclusion of the Ginkgolide B in the cavity of the β-cyclodextrin derivative. It can also be observed that Ginkgolide B only exists in the inclusion complex in the closed form at pH=4.9.

It should be noted that the solubility of the inclusion complex is the same at physiological pH, namely 2 mmole/L of Ginkgolide B in the presence of 20 mmole/L of the β-cyclodextrin derivative. With the inclusion complex prepared in the aforementioned manner, only two different forms are observed in identical proportions, including the closed form. When the Ginkgolide B is in the form of an inclusion complex, at pH 4.9, and with a concentration of 2 mmole/L in the presence of 20 mmole/L of 6-S-α-maltosyl-6-thiocyclo-maltoheptaose, there is a closed form concentration 20 times higher than that contained in the injectable formulation (2 and 0.1 mmole/L respectively) whereas the total Ginkgolide B concentration is lower (2 and 40 mmole/L respectively).

We claim:

1. A process for solubilization in an aqueous medium of an antagonizing agent of the platelet aggregation factor belonging to the family of Ginkgolides, characterized in that it consists of combining said agent with a cyclodextrin of formula:

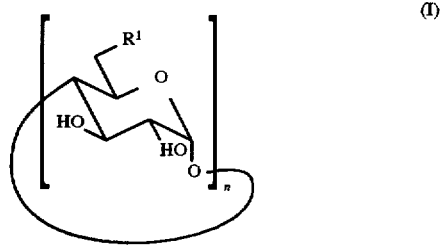

(I)

in which n is equal to 6, 7 or 8 and the $R^1$, which can be the same or different, represent OH or $SR^2$, with $R^2$ representing a group derived from a monosaccharide or an oligosaccharide, in order to form therewith an inclusion complex soluble in water.

2. The process according to claim 1, characterized in that $R^2$ complies with the formula:

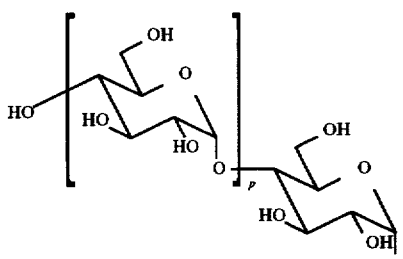

in which p is equal to 0 or an integer from 1 to 5.

3. The process according to claim 1, characterized in that the antagonizing agent comprises a Ginkgolide of formula:

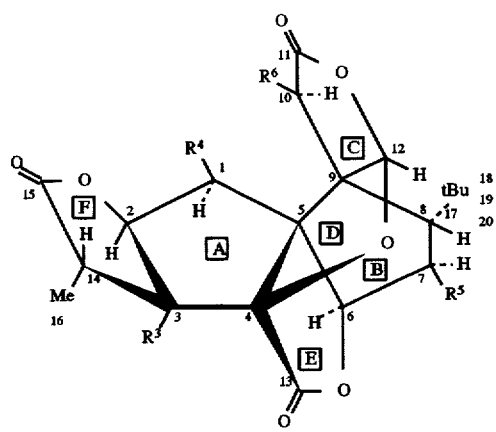

in which $R^3$, $R^5$ and $R^6$, which can be the same or different, represent H or OH, and $R^4$ represents H, OH or an alkoxy group with 1 to 5 carbon atoms.

4. The process according to claim 3, characterized in that $R^3$, $R^4$ and $R^6$ represent OH and $R^5$ represents H.

5. The process according to claim 1, characterized in that all the $R^1$ represent OH.

6. The process according to claim 1, characterized in that one of the $R^1$ represents $SR^2$ with $R^2$ being an α-maltosyl or β-maltosyl group, the other $R^1$ representing OH.

7. The process according to claim 1, characterized in that n is equal to 7 or 8.

8. The process according to claim 2, characterized in that the antagonizing agent comprises a Ginkgolide of formula:

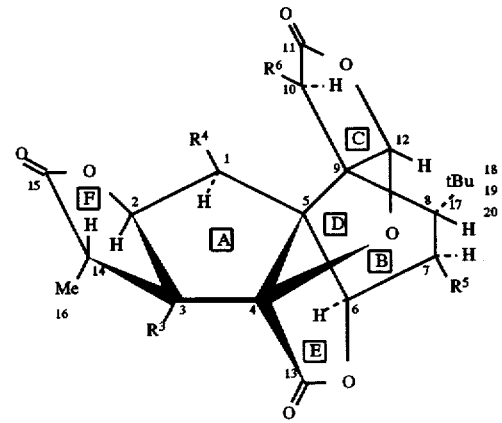

in which $R^3$, $R^5$ and $R^6$, which can be the same or different, represent H or OH and $R^4$ represents H, OH or an alkoxy group with 1 to 5 carbon atoms.

9. The process according to claim 1, characterized in that $R^3$, $R^4$ and $R^6$ represents OH and $R^5$ represents H.

10. The process according to claim 3, characterized in that all the $R^1$ represent OH.

11. The process according to claim 3, characterized in that one of the $R^1$ represents $SR^2$ with $R^2$ being an α-maltosyl or β-maltosyl group, the other $R^1$ representing OH.

12. The process according to claim 3, characterized in that n is equal to 7 or 8.

13. An inclusion complex of an antagonizing agent of the platelet aggregation factor belonging to the family of Ginkgolides in a cyclodextrin of formula:

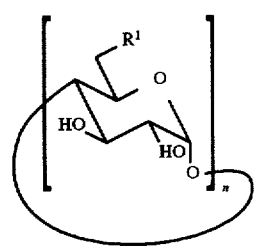

in which n is equal to 6, 7 or 8 and the $R^1$, which can be the same or different, represent OH or $SR^2$, with $R^2$ representing a group derived from a monosaccharide or an oligosaccharide.

14. Complex according to claim 13, characterized in that $R^2$ complies with formula (II):

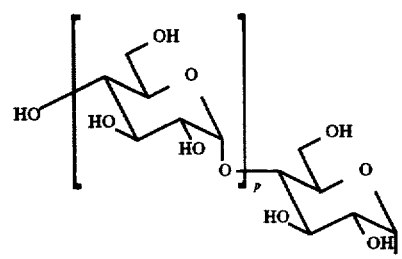

in which p is equal to 0 or an integer from 1 to 5.

15. Complex according to claim 13, characterized in that the antagonizing agent complies with the formula:

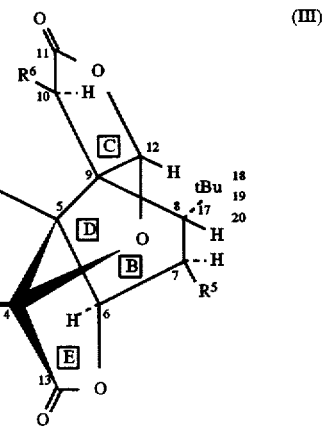

in which $R^3$, $R^5$ and $R^6$, which can be the same or different, represent H or OH or an alkoxy group with 1 to 5 carbon atoms.

16. Complex according to claim 15, characterized in that $R^3$, $R^4$ and $R^6$ represent OH and $R^5$ represents H.

17. Complex according to claim 13, characterized in that all the $R^1$ represent OH and n is equal to 7 or 8.

18. Complex according to claim 13, characterized in that n is equal to 7 and one of the $R^1$ represents $SR^2$ with $R^2$ being the α-maltosyl group.

19. Complex according to claim 13, characterized in that the antagonizing agent complies with the formula:

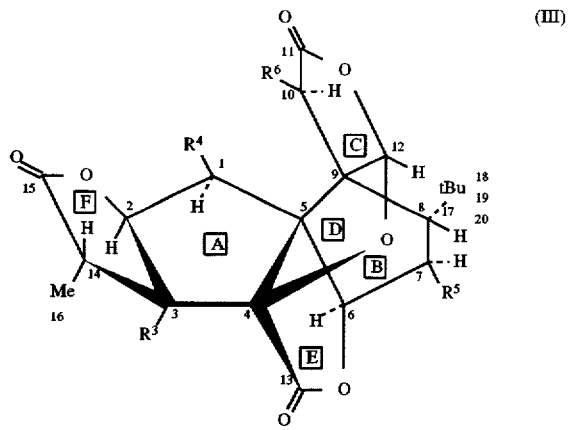

(III)

in which $R^3$, $R^5$ and $R^6$, which can be the same or different, represent H or OH, and $R^4$ represents H, OH or an alkoxy group with 1 to 5 carbon atoms.

20. Complex according to claim 19, characterized in that $R^3$, $R^4$ and $R^6$ represent OH and $R^5$ represents H.

21. Complex according to claim 19, characterized in that all the $R^1$ represents OH and n is equal to 7 or 8.

22. Complex according to claim 19, characterized in that n is equal to 7 and one of the $R^1$ represents $SR^2$ with $R^2$ being the α-maltosyl group.

23. A pharmaceutical composition, characterized in that it comprises an inclusion complex according to claim 13 with a pharmaceutically acceptable vehicle.

24. A pharmaceutical composition, characterized in that it comprises an inclusion complex according to claim 19 with a pharmaceutically acceptable vehicle.

\* \* \* \* \*